United States Patent
Yang et al.

(10) Patent No.: US 12,285,448 B2
(45) Date of Patent: Apr. 29, 2025

(54) BIFIDOBACTERIUM BREVE CAPABLE OF RELIEVING RHEUMATOID ARTHRITIS AND APPLICATION THEREOF

(71) Applicant: Jiangnan University, Wuxi (CN)

(72) Inventors: Bo Yang, Wuxi (CN); Wei Chen, Wuxi (CN); Zhexin Fan, Wuxi (CN); Qixiao Zhai, Wuxi (CN); Gang Wang, Wuxi (CN); Wenwei Lu, Wuxi (CN); Shumao Cui, Wuxi (CN); Jianxin Zhao, Wuxi (CN); Hao Zhang, Wuxi (CN)

(*) Notice: Subject to any disclaimer, the term of this patent is extended or adjusted under 35 U.S.C. 154(b) by 498 days.

(21) Appl. No.: 17/696,959

(22) Filed: Mar. 17, 2022

(65) Prior Publication Data

US 2022/0211776 A1 Jul. 7, 2022

Related U.S. Application Data

(63) Continuation of application No. PCT/CN2021/107916, filed on Jul. 22, 2021.

(30) Foreign Application Priority Data

Sep. 3, 2020 (CN) .......................... 202010913384.1

(51) Int. Cl.
| | | |
|---|---|---|
| A61K 35/745 | (2015.01) | |
| A23L 2/52 | (2006.01) | |
| A23L 33/00 | (2016.01) | |
| A23L 33/135 | (2016.01) | |
| A61P 19/02 | (2006.01) | |

(52) U.S. Cl.
CPC .............. *A61K 35/745* (2013.01); *A23L 2/52* (2013.01); *A23L 33/135* (2016.08); *A23L 33/40* (2016.08); *A61P 19/02* (2018.01); *A23V 2002/00* (2013.01); *A23V 2400/519* (2023.08)

(58) Field of Classification Search
CPC ....... A61K 35/745; A23L 2/52; A23L 33/135; A61P 19/02; A23V 2002/00; A23V 2400/51; A23V 2400/519
See application file for complete search history.

(56) References Cited

FOREIGN PATENT DOCUMENTS

| CN | 1863540 A | 11/2006 |
|---|---|---|
| CN | 103037875 A | 4/2013 |
| CN | 112111424 A | 12/2020 |
| EP | 3194567 A1 | 7/2017 |

OTHER PUBLICATIONS

Celik et al., J dairy Sci., 2012, vol. 96, p. 3506-3516. dx.doi.org/10.3168/jds.2012-6327. (Year: 2012).*
Sajan Chandrangadhan Achi et. al., "Prophylactic effects of probiotic *Bifidobacterium* spp. in the resolution of inflammation in arthritic rats", Applied microbial and cell physiology, V103, p. 6287-6296. Jun. 5, 2019.

* cited by examiner

*Primary Examiner* — Kade Ariani
(74) *Attorney, Agent, or Firm* — IPRO, PLLC; Na Xu

(57) ABSTRACT

Described is a *B. breve* strain for relieving rheumatoid arthritis and application thereof, belonging to the technical field of microorganisms. Described is a *B. breve* strain CCFM1078 possessing the effect of relieving rheumatoid arthritis, and shown to: promote secretion of anti-inflammatory factor IL-10 from RAW264.7 cells; reduce joint thickness, clinical score, and incidence of rats with rheumatoid arthritis; decrease levels of the pro-inflammatory cytokines TNFα and IL-1β in the serum of rats with rheumatoid arthritis; regulate the content of short-chain fatty acids in the feces of rats with rheumatoid arthritis; decrease the proportion of Th17 cells in the mesenteric lymph nodes of rats with rheumatoid arthritis; and reduce secretion of pro-inflammatory factor IL-6 from synovial cells.

6 Claims, 7 Drawing Sheets
Specification includes a Sequence Listing.

BIFIDOBACTERIUM BREVE CAPABLE OF RELIEVING RHEUMATOID ARTHRITIS AND APPLICATION THEREOF

TECHNICAL FIELD

The disclosure relates to a *Bifidobacterium breve* strain capable of relieving rheumatoid arthritis and application thereof, and belongs to the technical field of microorganisms.

BACKGROUND

Rheumatoid arthritis (RA) is a complex autoimmune disease, mainly pathologically characterized in synovitis of the joints, deterioration to cartilage, bone tissue destruction, and eventually joint ankylosis and dysfunction. The incidence of rheumatoid arthritis (RA) is higher in women than in men, and higher in middle-aged and elderly people than in young children, and presents a certain heredity.

At this stage, in the treatment of rheumatoid arthritis, traditional drugs such as anti-rheumatic drugs, glucocorticoids, and non-steroidal anti-inflammatory drugs, as well as some new biological agents are often used. All these drugs have limitations. For example, at the initial stage of a disease, traditional drugs are used clinically to limit the disease, but these drugs can damage the liver, the kidney, and the gastrointestinal tract. When the therapeutic effect of the traditional drugs decreases or adverse responses occur, some biological agents targeting inflammatory factors such as IL-6 or TNFα are often used. These biological agents have good effects in the clinical short-term application, but their cost is high and the storage conditions are harsh. In addition, biological agents result in a cascade reaction forcibly preventing immune inflammation in the body, will cause a patient's immune system to be excessively suppressed by long-term use, and have a risk of inducing other diseases.

In terms of the prevention of rheumatoid arthritis, there is no clinically clear preventive drug for rheumatoid arthritis. This is because the pathogenesis of rheumatoid arthritis is complicated and involves not only immunity and genetics, but also symbiotic bacteria in the body. Among them, an abnormal immune response not only exists in joint lesions, but also manifests in other immune organs of the body. For example, in recent years, analysis of synovial fluid samples from the joint cavity of patients with rheumatoid arthritis has found that the level of pro-inflammatory factors and the proportion of Th17 cells are significantly higher than those of healthy people, and Th17 cells play a key role in the production of the pro-inflammatory factors. Animal experiments have also confirmed that Th17 cells in the intestinal mucosa of mice with rheumatoid arthritis are closely related to the occurrence and development of a disease (see the paper Microbiota-Dependent Involvement of Th17 Cells in Murine Models of Inflammatory Arthritis).

As an important immune site, the intestine contains a large number of intestinal microorganisms. These microorganisms not only affect the local immune response of the intestine, but also participate in the systemic immune response. Differentiation and development of Th17 cells require the presence and stimulation of intestinal microorganisms. Therefore, how to reduce Th17 cells with the intestine as a target is an important idea to prevent rheumatoid arthritis. In addition, an important feature of rheumatoid arthritis in the pathology is that synovial fibroblasts proliferate abnormally, migrate and even infect surrounding adjacent tissues, and can secrete a variety of inflammatory cytokines. Therefore, the response of synovial fibroblasts to external intervention is also an important evaluation index.

Probiotics are a type of bacteria that colonize a human body, change the composition of a host's intestinal flora, and then metabolize to produce beneficial metabolites such as short-chain fatty acids to have a beneficial impact on the host. Studies have found that short-chain fatty acids can affect the development and differentiation of immune cells and promote the formation of anti-inflammatory cells and cytokines. Moreover, compared with ordinary drugs, probiotics have the advantages of high safety and low cost. In addition, studies have shown that a small number of probiotics can indeed prevent and/or treat some special diseases. For example, in a patent application document with the publication number CN108220206A, *Bifidobacterium longum* YS108R can prevent and/or treat colitis very well. Therefore, it is critical to discover a probiotic strain capable of preventing and/or treating rheumatoid arthritis to defeat rheumatoid arthritis.

At present, some progress has been made in the application of probiotics in the prevention and/or treatment of rheumatoid arthritis. For example, in a patent application document with the publication number US10617725B2, *Bifidobacterium bifidum* KCTC13474BP can relieve rheumatoid arthritis. However, the mitigation of rheumatoid arthritis by the *B. bifidum* KCTC13474BP mainly focuses on an anti-inflammatory effect in cells in vitro and inhibition of rheumatoid arthritis autoantibodies, and there is still a lack of research on other indicators.

SUMMARY

Technical Problem

The technical problem to be solved by the disclosure is to provide a *B. breve* strain capable of relieving rheumatoid arthritis.

Technical Solution

To solve the technical problem of the disclosure, the disclosure provides a *B. breve* strain CCFM1078, the *B. breve* CCFM1078 was preserved at the Guangdong Microbial Culture Collection Center on May 6, 2020, with the preservation number GDMCC No:61011, and the preservation address is 5$^{th}$ Floor, Building 59, Grand Courtyard 100, Xianlie Middle Road, Guangzhou.

The *B. breve* CCFM1078 was isolated from feces samples of healthy babies from Wuxi. The strain was sequenced and analyzed, and the 16S rDNA sequence of the strain is as shown in SEQ ID NO.1. The sequence obtained by sequencing was subjected to nucleic acid sequence alignment in NCBI, and the result showed that the strain was *B. breve*, named *B. breve* CCFM1078.

A colony of the *B. breve* CCFM1078 on an MRS medium presents a milky white color, a smooth surface, and a round convexity.

The disclosure further provides a method for preparing a product for preventing and/or treating rheumatoid arthritis, the method using the above *B. breve* CCFM1078.

In one implementation of the disclosure, in the product, the viable count of the above *B. breve* CCFM1078 is not less than $1\times10^5$ CFU/mL or $1\times10^5$ CFU/g.

In one implementation of the disclosure, the product includes food products or medicines.

In one implementation of the disclosure, the medicine contains the above *B. breve* CCFM1078, a drug carrier and/or pharmaceutical excipients.

In one implementation of the disclosure, the food product includes a health food product containing the above *B. breve* CCFM1078.

In one implementation of the disclosure, the food product includes dairy products, bean products, meat products, or fruit and vegetable products produced by using a starter containing the above *B. breve* CCFM1078.

In one implementation, the product includes a freeze-dried bacterial powder or a starter containing the *B. breve*.

In one implementation of the disclosure, a preparation method of the starter includes: inoculating a medium with the above *B. breve* CCFM1078 according to an inoculation amount of 2-4% of the total mass of the medium, and culturing the bacteria at 37° C. for 18-24 h to obtain a culture solution; centrifuging the culture solution to obtain bacteria; and resuspending the bacteria with normal saline to obtain the starter.

In one implementation of the disclosure, the medium is an MRS medium.

In one implementation, the freeze-dried bacterial powder is prepared according to the following method:
(1) inoculating an MRS liquid medium with the *B. breve*, culturing the bacteria anaerobically at 30-37° C., and collecting bacterial cells;
(2) after washing the bacterial cells with sterile normal saline, resuspending the bacterial cells with a freeze-drying protectant containing trehalose to a concentration $\geq 5 \times 10^{10}$ CFU/mL to obtain a resuspension; and
(3) freeze-drying the resuspension by vacuum freezing to obtain a freeze-dried *B. breve* powder.

The disclosure further provides a product for preventing and/or treating rheumatoid arthritis, the product containing the above *B. breve* CCFM1078.

In one implementation of the disclosure, the prevention and/or treatment of rheumatoid arthritis includes at least one of the following effects:
(1) promoting cells to secrete anti-inflammatory factor IL-10;
(2) reducing the joint thickness, clinical score and incidence of individuals with rheumatoid arthritis;
(3) decreasing the levels of pro-inflammatory cytokines TNFα and IL-1β in the serum of individuals with rheumatoid arthritis;
(4) regulating the content of short-chain fatty acids in the feces of individuals with rheumatoid arthritis;
(5) decreasing the proportion of Th17 cells in the mesenteric lymph nodes of individuals with rheumatoid arthritis; and
(6) reducing the secretion of pro-inflammatory factor IL-6 from synovial cells of individuals with rheumatoid arthritis.

In one implementation of the disclosure, in the product, the viable count of the above *B. breve* CCFM1078 is not less than $1 \times 10^5$ CFU/mL or $1 \times 10^5$ CFU/g.

In one implementation of the disclosure, the product includes food products or medicines.

In one implementation of the disclosure, the medicine contains the above *B. breve* CCFM1078, a drug carrier and/or pharmaceutical excipients.

In one implementation of the disclosure, the food product includes a health food product containing the above *B. breve* CCFM1078; or the food product includes dairy products, bean products, meat products, or fruit and vegetable products produced using a starter of the above *B. breve* CCFM1078.

The disclosure further provides application of the *B. breve* or a product containing the *B. breve* in the prevention and/or treatment of rheumatoid arthritis.

In one implementation, in the application, the *B. breve* or the product containing the *B. breve* is ingested into the gastrointestinal tract of a mammal.

Beneficial Effects

1. The disclosure screens out a *B. breve* strain CCFM1078, and the *B. breve* CCFM1078 has the effect of relieving rheumatoid arthritis, being specifically embodied in:
(1) significantly promoting secretion of anti-inflammatory factor IL-10 from RAW264.7 cells;
(2) significantly reducing the joint thickness, clinical score and incidence of rats with rheumatoid arthritis;
(3) significantly decreasing the levels of pro-inflammatory cytokines TNFα and IL-1β in the serum of rats with rheumatoid arthritis;
(4) significantly regulating the content of short-chain fatty acids in the feces of rats with rheumatoid arthritis;
(5) significantly decreasing the proportion of Th17 cells in the mesenteric lymph nodes of rats with rheumatoid arthritis;
(6) significantly reducing the secretion of pro-inflammatory factor IL-6 from synovial cells.

Therefore, the *B. breve* CCFM1078 has great application prospects in the preparation of products (such as food products or medicines) for preventing and/or treating rheumatoid arthritis.

2. *B. breve* is a kind of probiotics, and has been included in the List of Bacteria that Can Be Used in Food product issued by the Ministry of Health. Therefore, the *B. breve* CCFM1078 screened by the disclosure will not bring any potential safety hazards to patients with rheumatoid arthritis (RA).

3. A culture process of *B. breve* only requires a medium and control of some culture conditions, and the cost is relatively low. Compared with expensive biological agents, the *B. breve* will not bring too much economic burden to patients with rheumatoid arthritis (RA).

Biomaterial Preservation

A *B. breve* strain CCFM1078, with the taxonomic name of *B. breve*, was preserved at the Guangdong Microbial Culture Collection Center on May 6, 2020, with the preservation number GDMCC No:61011, and the preservation address is 5th Floor, Building 59, Grand Courtyard 100, Xianlie Middle Road, Guangzhou.

DETAILED DESCRIPTION

Figure 1:
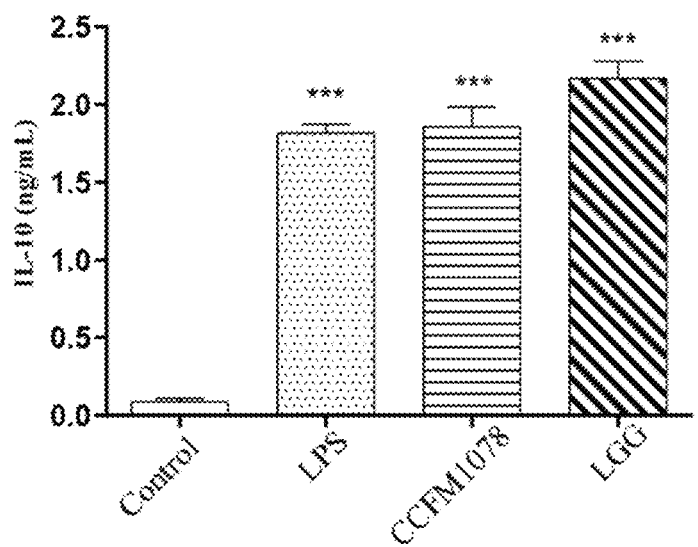
FIG. 1 shows the effect of the *B. breve* CCFM1078 on the secretion of anti-inflammatory factor IL-10 from RAW264.7 cells.

The disclosure will be further explained with specific examples and accompanying drawings below.

Pepsin (product number: A610411), trypsin (product number: A610629), and bile salt (product number: A600225) involved in the following examples were purchased from Sangon Biotech (Shanghai) Co., Ltd. *Lactobacillus rhamnosus* GG (LGG) involved in the following examples was purchased from the American Type Culture Collection (ATCC). RAW264.7 cells involved in the following examples were purchased from the Cell Bank of the Chinese Academy of Sciences (Shanghai). Fetal bovine serum and DEME complete media involved in the following examples were purchased from Life Technologies. Endotoxin (LPS) involved in the following examples was purchased from Sigma. Methotrexate involved in the following examples was purchased from Sangon Biotech (Shanghai) Co., Ltd. A bovine type II collagen solution and a Freund's incomplete adjuvant involved in the following examples were purchased from Chondrex. ELISA kits for detecting IL-1β (article number: DY501), IL-10 (article number: DY522), TNFα (article number: DY510) and IL-6 (article number: DY506) involved in the following examples were purchased from R&D.

The Media Involved in the Following Examples are as Follows:

MRS solid medium: Peptone 10 g/L, beef extract 10 g/L, glucose 20 g/L, sodium acetate 2 g/L, yeast powder 5 g/L, diammonium hydrogen citrate 2 g/L, $K_2PO_4 \cdot 3H_2O$ 2.6 g/L, $MgSO_4 \cdot 7H_2O$ 0.1 g/L, $MnSO_4$ 0.05 g/L, Tween 80 1 mL/L, agar 20 g/L, and cysteine hydrochloride 0.5 g/L.

MRS liquid medium: Peptone 10 g/L, beef extract 10 g/L, glucose 20 g/L, sodium acetate 2 g/L, yeast powder 5 g/L, diammonium hydrogen citrate 2 g/L, $K_2PO_4 \cdot 3H_2O$ 2.6 g/L, $MgSO_4 \cdot 7H_2O$ 0.1 g/L, $MnSO_4$ 0.05 g/L, Tween 80 1 mL/L, and cysteine hydrochloride 0.5 g/L.

Example 1: Screening and Strain Identification of *B. breve* CCFM1078

1. Screening

A feces sample from healthy babies from Wuxi area was stored in 30% glycerin in a refrigerator at −80° C. After the sample was taken out and thawed at a low temperature, the sample was uniformly mixed. 0.5 mL of the sample was pipetted and added to 4.5 mL of normal saline, and gradient dilution was performed on the sample with 0.9 g/100 mL normal saline containing 0.05 g/100 mL cysteine. An appropriate gradient dilution was selected and spread on an MRS solid medium supplemented with 0.05 g/100 mL cysteine, and cultured at 37° C. for 48 h. Typical colonies were picked and streaked on an MRS solid medium for purification, and a single colony was picked and transferred to an MRS liquid medium (containing 0.05 g/100 mL cysteine) and cultured. The cultured bacteria were stored in 30% glycerin to obtain a strain CCFM1078.

2. Identification

The genome of the CCFM1078 was extracted, and the 16S rDNA of the CCFM1078 was amplified and sequenced (performance was done by Huada Gene Technology Co., Ltd., and the amplified nucleotide sequence of the 16S rDNA of the CCFM1078 is shown in SEQ ID NO.1). Nucleic acid sequence alignment of the sequence in NCBI showed that the strain was *B. breve*, named *B. breve* CCFM1078.

3. Genome Draft Information

The genome of the CCFM1078 was extracted, and the genome sequence was sequenced on the Illumina Hiseq sequencing platform to obtain original data of the whole genome draft. The genome of the *B. breve* CCFM1078 is 2.36 Mb, and the content of G+C % is 58.90%.

Example 2: Culture of *B. breve* CCFM1078

An MRS solid medium (containing 0.05 g/100 mL cysteine hydrochloride) was inoculated with the *B. breve* CCFM1078 obtained in Example 1 and cultured in an anaerobic incubator at 37° C. for 48 h. The colony was observed, and it was found that the colony was milky white, with a smooth surface and round convexity.

An MRS liquid medium (containing 0.05 g/100 mL cysteine hydrochloride) was inoculated with the *B. breve* CCFM1078 obtained in Example 1 and anaerobically cultured at 37° C. for 18 h, and then transferred into a fresh MRS liquid medium (containing 0.05 g/100 mL cysteine) and cultured at same conditions for 24 h. Bacteria were centrifuged at 6000 g for 15 min, washed with 0.9 g/100 mL normal saline and recentrifuged at 6000 g for 10 min to obtain bacteria. The bacteria were resuspended with a 30% sucrose solution and cryopreserved at −80° C. for later use.

Example 3: Tolerance of *B. breve* CCFM1078 to Simulated Gastrointestinal Fluid

1. Tolerance of *B. breve* CCFM1078 to Simulated Gastric Liquid

An MRS liquid medium was inoculated with the *B. breve* CCFM1078 obtained in Example 1 and cultured anaerobically at 37° C. for 24 h, and the cells were collected by centrifugation. The collected cells were washed with normal saline. After washing, the cells were collected by centrifugation. The collected cells were resuspended in normal saline containing 3 g/L pepsin, with a pH of 3 (the pH was adjusted by HCl). 0.1 mL of the bacterial solution was taken to count viable bacteria on a plate by a pouring method as the original viable count of the *B. breve* CCFM1078 in the bacterial solution. The remaining bacterial solution was anaerobically cultured at 37° C. for 3 h, and then 0.1 mL of the bacterial solution was taken to count viable bacteria on a plate by the pouring method as the viable count of the *B. breve* CCFM1078 in the bacterial solution after tolerating simulated gastric liquid. The survival rate of the *B. breve* CCFM1078 after tolerating the gastric liquid was calculated, where the survival rate after tolerating the gastric liquid (%)=(the viable count of *B. breve* in the bacterial solution after tolerating the simulated gastric liquid/the original viable count of *B. breve* in the bacterial solution)×100%.

The calculation result is that the survival rate of the *B. breve* CCFM1078 after tolerating the gastric liquid was as high as 67%.

2. Tolerance of *B. breve* CCFM1078 to Simulated Intestinal Liquid

An MRS liquid medium was inoculated with the *B. breve* CCFM1078 obtained in Example 1 and cultured anaerobically at 37° C. for 24 h, and the cells were collected by centrifugation. The collected cells were washed with normal saline. After washing, the cells were collected by centrifugation. The collected cells were resuspended in normal saline containing 1 g/L trypsin and 0.3 g/L bile salt, with a pH of 8 (the pH was adjusted by NaOH). 0.1 mL of the bacterial solution was taken to count viable bacteria on a plate as the original viable count of the *B. breve* in the bacterial solution. The remaining bacterial solution was anaerobically cultured at 37° C. for 4 h, and then 0.1 mL of the bacterial solution was taken to count viable bacteria on a plate by the pouring method as the viable count of the *B. breve* in the bacterial solution after tolerating simulated intestinal liquid. The survival rate of the *B. breve* CCFM1078 after tolerating the intestinal liquid was calculated, where the survival rate after tolerating the intestinal liquid (%)=(the viable count of *B. breve* in the bacterial solution after tolerating the simulated intestinal liquid/the original viable count of *B. breve* in the bacterial solution)×100%.

The calculation result is that the survival rate of the *B. breve* CCFM1078 after tolerating the intestinal liquid was as high as 11.78%.

In conclusion, the *B. breve* CCFM1078 has strong tolerance to simulated gastric liquid and simulated intestinal liquid.

Example 4: Effect of *B. breve* CCFM1078 on the Secretion of Anti-Inflammatory Factor IL-10 from RAW264.7 Cells The RAW264.17 cell strain stored in liquid nitrogen was taken out and thawed at 37° C. The frozen stock solution was transferred to 5 mL of a DEME complete medium to obtain a mixed solution. The mixed solution was centrifuged at 1000 g for 5 min and the supernatant was discarded to obtain pellets. The pellets were added to 10 mL of a DEME complete medium containing 10% (v/v) fetal bovine serum, pipetted evenly, transferred to a cell culture dish, and cultured in a cell incubator at 37° C. In the culture process, the cell state was observed under a microscope. When the cells in the culture dish grew adherently and had good morphology, and the culture dish was about 80% full, the medium was carefully aspirated. 0.25 g/100 mL trypsin was added to the culture dish for digestion for 3 min. After the digestion, 2 mL of a DEME complete medium was added to the culture dish to stop the digestion, the cells were gently pipetted to be detached, and a cell suspension A was collected. The cell suspension A was centrifuged at 1000 g for 5 min and the supernatant was discarded to obtain cell pellets. The pellets were pipetted evenly with 10 mL of the DEME complete medium containing 10% (v/v) fetal bovine serum for counting, and the cell concentration was adjusted to $5 \times 10^6$ cells/mL with the DEME complete medium containing 10% (v/v) fetal bovine serum to obtain a cell suspension B. The cell suspension B was transferred to a new culture dish and cultured in a cell incubator at 37° C. for 24 h, and then the medium was carefully aspirated. The cells were washed with a sterile PBS buffer to remove non-adherent cells, and adherent RAW264.17 cells were obtained.

MRS liquid media (containing 0.05 g/100 mL cysteine) were respectively inoculated with the *B. breve* CCFM1078 obtained in Example 1 and LGG and anaerobically cultured at 37° C. for 18 h, and then transferred into fresh MRS liquid media (containing 0.05 g/100 mL cysteine) and cultured at same conditions for 24 h. Bacteria were centrifuged at 6000 g for 15 min, washed with 0.9 g/100 mL normal saline, and centrifuged again at 6000 g for 10 min to obtain the bacteria. The bacteria of the *B. breve* CCFM1078 and the LGG were resuspended to a bacterial concentration of $5 \times 10^6$ cells/mL with DEME complete media, and complete DEME media containing the *B. breve* CCFM1078 and the LGG were obtained.

The adherent RAW264.17 cells were divided into four groups, namely a blank group, an LPS positive group, a CCFM1078 group and an LGG group. 1 mL of a DEME complete medium was added to the adherent RAW264.17 cells in the blank group, 1 mL of a DEME complete medium was added to the adherent RAW264.17 cells in the LPS positive group, 1 mL of a DEME complete medium containing the *B. breve* CCFM1078 was added to the adherent RAW264.17 cells in the CCFM1078 group, and 1 mL of a DEME complete medium containing the LGG was added to the adherent RAW264.17 cells in the LGG group, and the cells were cultured in a cell incubator (37° C., 5% $CO_2$) for 4 h. 1 mL of a 200 ng/mL LPS solution was added to the adherent RAW264.17 cells in the LPS positive group, the CCFM1078 group and the LGG group, respectively, 1 mL of a DEME complete medium was added to the blank group, and the cells were cultured in a cell culture incubator (37° C., 5% $CO_2$) for 48 h to obtain culture solutions.

The culture solution was centrifuged to take the supernatant, and the level of IL-10 in the supernatant was determined. Determination was repeated six times for each group (see FIG. 1 for the determination results).

It can be seen from FIG. 1 that after LPS stimulation, the secretion of IL-10 from the RAW264.17 cells significantly increased (up to 1.8 ng/mL), while both the *B. breve* CCFM1078 and the LGG could further increase the secretion of IL-10 from the RAW264.17 cells (up to 1.9 ng/mL and 2.2 ng/mL, respectively), indicating that both the *B. breve* CCFM1078 and the LGG could promote secretion of anti-inflammatory factors in vitro.

A Type II Collagen-induced arthritis (CIA) model is a classic RA animal model. The onset of CIA has many similarities with rheumatoid arthritis (RA), such as synovial hyperplasia, pannus formation, and cartilage destruction. At present, LGG is mainly used clinically to treat rheumatoid arthritis (RA). Therefore, in Examples 5-9, a type II collagen-induced arthritis (CIA) model was used as an RA animal model, and LGG was used as a control.

In Examples 5-9, the bacterial solution preparation methods of the *B. breve* CCFM1078 and the LGG were as follows:

MRS liquid media (containing 0.05 g/100 mL cysteine) were respectively inoculated with the *B. breve* CCFM1078 obtained in Example 1 and LGG and anaerobically cultured at 37° C. for 18 h, and then transferred into fresh MRS liquid media (containing 0.05 g/100 mL cysteine) and cultured at same conditions for 24 h. Bacteria were centrifuged at 6000 g for 15 min, washed with 0.9 g/100 mL normal saline, and centrifuged again at 6000 g for 10 min to obtain the bacteria. The bacteria of the *B. breve* CCFM1078 and the LGG were resuspended to a cell concentration of $5 \times 10^9$ CFU/mL with sterile normal saline with a concentration of 0.9 g/100 mL, and bacterial solutions containing the *B. breve* CCFM1078 and the LGG were obtained.

Example 5: Effect of *B. breve* CCFM1078 on Body Weight, Joint Thickness, Clinical Score and Incidence of Rats with Rheumatoid Arthritis 60 7-week-old SPF (Specific Pathogen Free) female Wistar rats were raised at a room temperature of 22-24° C., a humidity of 40-60%, and an alternation of 12 h/12 h day and night. After being raised for 1 week under the condition of ad libitum, the rats were randomly divided into 5 groups with 12 rats in each group. The 5 groups were a normal group, a model group, a drug group administered with methotrexate by gavage, an LGG group administered with LGG by gavage, and a CCFM1078 group administered with *B. breve* CCFM1078 by gavage.

The experiment was started after the rats were adaptively raised for one week, and lasted for eight weeks. During the two weeks before modelling, each rat in the normal group, the drug group and the model group was administered by gavage with 1.5 mL of sterile normal saline with a concentration of 0.9 g/100 mL per day, each rat in the LGG group was administered by gavage with 1.5 mL of an LGG bacterial solution with a concentration of $5 \times 10^9$ CFU/mL per day, and each rat in the CCFM1078 group was administered by gavage with 1.5 mL of a *B. breve* CCFM1078 bacterial solution with a concentration of $5 \times 10^9$ CFU/mL per day. The third week to the fourth week was a modelling period. On the first day of modelling, a bovine type II collagen solution (Chondrex, 20022) and a Freund's incomplete adjuvant (Chondrex, 7002) were mixed in equal volumes and emulsified to form a complete emulsion (the emulsion was prepared for immediate use, and the prepared emulsion was used within 1 h). A rat was anesthetized with isoflurane and immobilized, the whole rat tail root was disinfected with 75% (v/v) alcohol, and then the rat was subjected to primary immunization. In the primary immunization, 0.15 mL of the complete emulsion was accurately pipetted and injected subcutaneously at 1.5 cm from the tail root of the rat. One week later, booster immunization was conducted by the same treatment method, that is, 0.15 mL of the complete emulsion was accurately pipetted and injected subcutaneously at 2.0 cm from the tail root of the rat. The rats in the normal group were injected with only the same volume of sterile normal saline by the same method. During the modelling until the end of the experiment, each rat in the normal group and the model group was administered by gavage with 1.5 mL of sterile normal saline with a concentration of 0.9 g/100 mL per day; the drug group was administered by gavage with methotrexate twice at a dose of 7.6 mg/kg based on body weight, and was administered with 1.5 mL of sterile normal saline with a concentration of 0.9 g/100 mL for the rest of the time; each rat in the LGG group was administered by gavage with 1.5 mL of an LGG bacterial solution with a concentration of $5 \times 10^9$ CFU/mL per day; and each rat in the CCFM1078 group was administered by gavage with 1.5 mL of a *B. breve* CCFM1078 bacterial solution with a concentration of $5 \times 10^9$ CFU/mL per day.

During and after modeling, the body weight of the rats in each group was measured by a weight scale, the joint thickness of the rats in each group was measured by a micrometer caliper, and the clinical scores of the rats in each group were determined by observing the degrees of swelling, redness and stiffness of the ankles and knuckles (see Reference: Shan, J., et al., *Integrated Serum and Fecal Metabolomics Study of Collagen-Induced Arthritis Rats and the Therapeutic Effects of the Zushima Tablet*. Front Pharmacol, 2018. 9: p. 891. for details). The determination results are shown in FIGS. 2-4.

Figure 2:
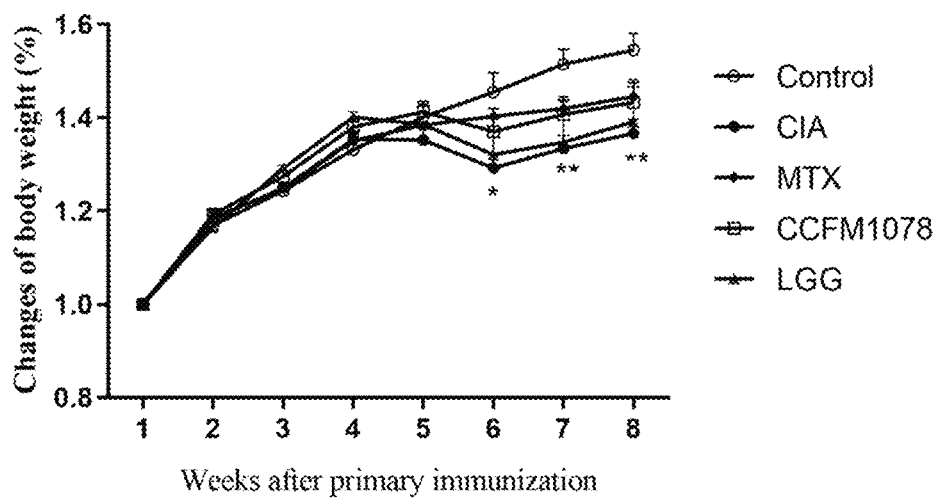
FIG. 2 shows the effect of the *B. breve* CCFM1078 on the body weight of rats with rheumatoid arthritis.
Figure 3:
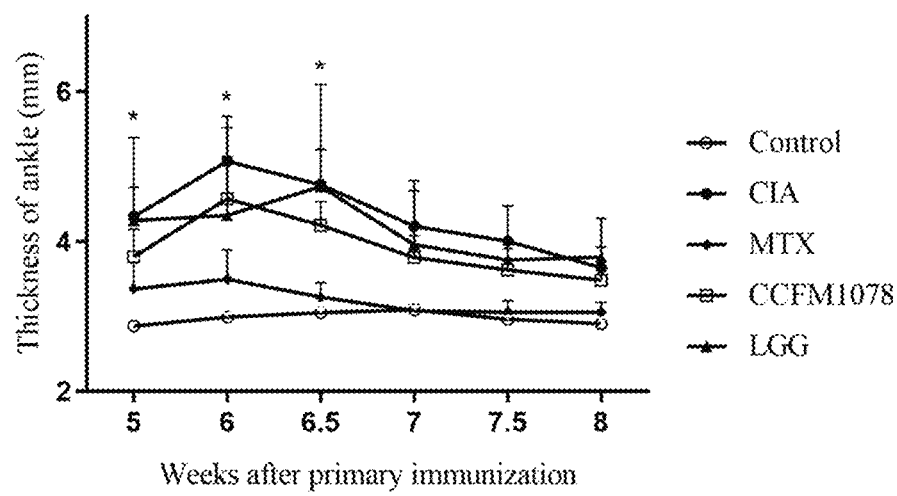
FIG. 3 shows the effect of the *B. breve* CCFM1078 on the thickness of paw joints of rats with rheumatoid arthritis.

From FIG. 2, after the booster immunization, the body weight gain rate of the rats in the model group decreased in the first two weeks, and the body weight at the sixth week was close to the body weight before the modeling (the $3^{rd}$ week) (the body weight was 1.292 and 1.249 times the initial body weight, respectively); the body weight gain was restored in the last two weeks, but the body weight gain rate was significantly lower than that of the rats in the normal group in the same period. The body weight change of the rats in the drug group was not significant. The body weight change trend of the rats in the LGG group and the CCFM1078 group was similar to that of the model group, but the body weight gain rate of the rats in the CCFM1078 group was equivalent to that of the drug group.

From FIG. 3, 1 week after the booster immunization, the joints and paws of the rats in the model group began to swell, and the thickness of the paws of the rats in the model group was significantly greater than that of the rats in the normal group in the following 10 days. The paw thickness of the rats in the drug group was significantly lower than that of the rats in the model group and restored to normal in the last week. The change trend of paw joint swelling of the rats in the CCFM1078 group was consistent with the changes in the rats in the model group, but the average paw thickness of the rats in the CCFM1078 group was less than that of the rats in the model group, where in the 5th, 6th and 6.5th weeks of the experiment, the average paw thickness of the rats in the CCFM1078 group was only 87.5%, 90.1% and 88.6% of that of the rats in the model group. In the same period, the paw thickness of the rats in the CCFM1078 group was less than that of the rats in the LGG group.

Figure 4:
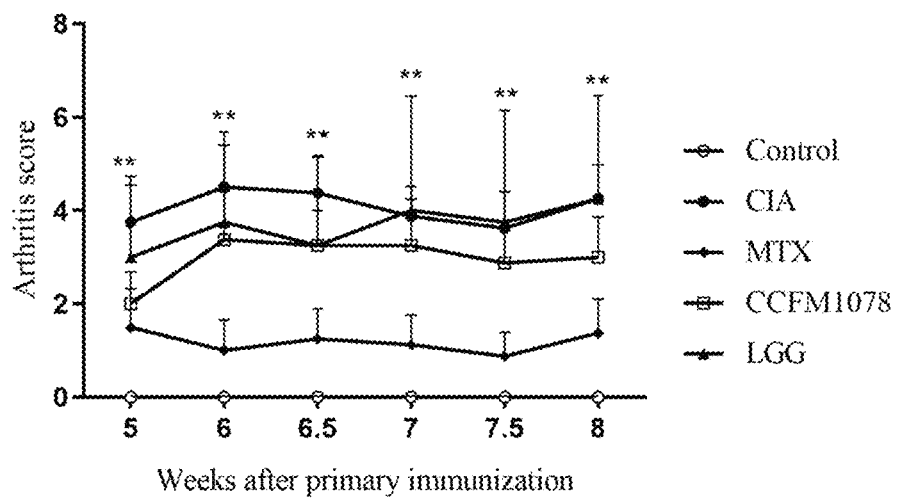
FIG. 4 shows the effect of the *B. breve* CCFM1078 on the clinical score of rats with rheumatoid arthritis.

From FIG. 4, the changes in the clinical scores of the rats in each group were similar to the change curves of the paw joint thickness. 1 week after the booster immunization, the clinical scores of the rats in the model group were significantly higher than those of the rats in the normal group and the drug group. The clinical scores of the rats in the CCFM1078 group were lower than those of the rats in the model group. Starting from the 6th week of the experiment, the clinical scores of the rats in the CCFM1078 group began to stabilize and were lower than those of the LGG group, where in the 5th, 6th and 6.5th weeks of the experiment, the clinical scores of the rats in the CCFM1078 group were only 53.3%, 75.0% and 74.2% of those of the model group. At the same time point, the clinical scores of the rats in the CCFM1078 group were lower than those of the LGG group but higher than those of the drug group.

It can be seen that the *B. breve* CCFM1078 could treat and prevent rheumatoid arthritis, and had good effects in relieving body weight loss and paw swelling caused by rheumatoid arthritis and decreasing clinical scores of rheumatoid arthritis. Although the effects were weaker than the drug methotrexate, the effects were stronger than the control bacteria LGG. Long-term use of the drug methotrexate has side effects, such as gastrointestinal reactions (diarrhea, nausea, etc.), and liver and kidney damage.

Example 6: Effect of *B. breve* CCFM1078 on the Levels of IL-1β and TNFα in the Serum of Rats with Rheumatoid Arthritis 60 7-week-old SPF (Specific Pathogen Free) female Wistar rats were raised at a room temperature of 22-24° C., a humidity of 40-60%, and an alternation of 12 h/12 h day and night. After being raised for 1 week under the condition of ad libitum, the rats were randomly divided into 5 groups with 12 rats in each group. The 5 groups were a normal group, a model group, a drug group administered with methotrexate by gavage, an LGG group administered with LGG by gavage, and a CCFM1078 group administered with *B. breve* CCFM1078 by gavage.

The experiment was started after the rats were adaptively raised for one week, and lasted for eight weeks. During the two weeks before modelling, each rat in the normal group, the drug group and the model group was administered by gavage with 1.5 mL of sterile normal saline with a concentration of 0.9 g/100 mL per day, each rat in the LGG group was administered by gavage with 1.5 mL of an LGG bacterial solution with a concentration of $5 \times 10^9$ CFU/mL per day, and each rat in the CCFM1078 group was administered by gavage with 1.5 mL of a *B. breve* CCFM1078 bacterial solution with a concentration of $5 \times 10^9$ CFU/mL per day. The third week to the fourth week was a modelling period. On the first day of modelling, a bovine type II collagen solution (Chondrex, 20022) and a Freund's incomplete adjuvant (Chondrex, 7002) were mixed in equal volumes and emulsified to form a complete emulsion (the emulsion was prepared for immediate use, and the prepared emulsion was used within 1 h). A rat was anesthetized with isoflurane and immobilized, the whole rat tail root was disinfected with 75% (v/v) alcohol, and then the rat was subjected to primary immunization. In the primary immunization, 0.15 mL of the complete emulsion was accurately pipetted and injected subcutaneously at 1.5 cm from the tail root of the rat. One week later, booster immunization was conducted by the same treatment method, that is, 0.15 mL of the complete emulsion was accurately pipetted and injected subcutaneously at 2.0 cm from the tail root of the rat. The rats in the normal group were injected with only the same volume of sterile normal saline by the same method. During the modelling until the end of the experiment, each rat in the normal group and the model group was administered by gavage with 1.5 mL of sterile normal saline with a concentration of 0.9 g/100 mL per day; the drug group was administered by gavage with methotrexate twice at a dose of 7.6 mg/kg based on body weight, and was administered with 1.5 mL of sterile normal saline with a concentration of 0.9 g/100 mL for the rest of the time; each rat in the LGG group was administered by gavage with 1.5 mL of an LGG bacterial solution with a concentration of $5 \times 10^9$ CFU/mL per day; and each rat in the CCFM1078 group was administered by gavage with 1.5 mL of a *B. breve* CCFM1078 bacterial solution with a concentration of $5 \times 10^9$ CFU/mL per day.

Four weeks after the booster immunization, blood was collected and the rats were sacrificed. The rat serum was collected, and the levels of IL-1β and TNFα in the serum of the rats in each group were determined by an ELISA kit. The detection results are shown in FIGS. 5-6.

Figure 5:
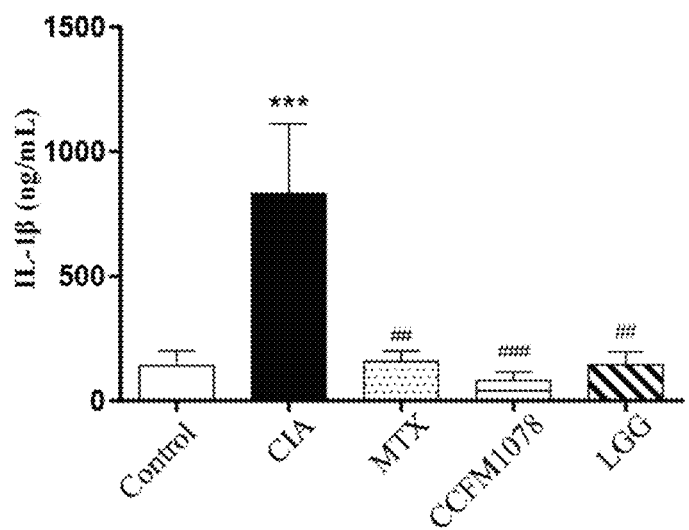
FIG. 5 shows the effect of the *B. breve* CCFM1078 on the level of IL-1β in the serum of rats with rheumatoid arthritis.

As shown in FIG. 5, the average concentration of IL-1β in the serum of the rats in the model group was 835 ng/L, and was significantly higher than that in the normal group (143 ng/L). Compared with the rats in the model group, the levels of IL-1β in the serum of the rats in the LGG group and the CCFM1078 group significantly decreased, and were 17.37% and 9.94% of that in the model group respectively. The level of IL-1β (159 ng/L) in the serum of the rats in the drug group was also significantly lower than that in the model group.

Figure 6:
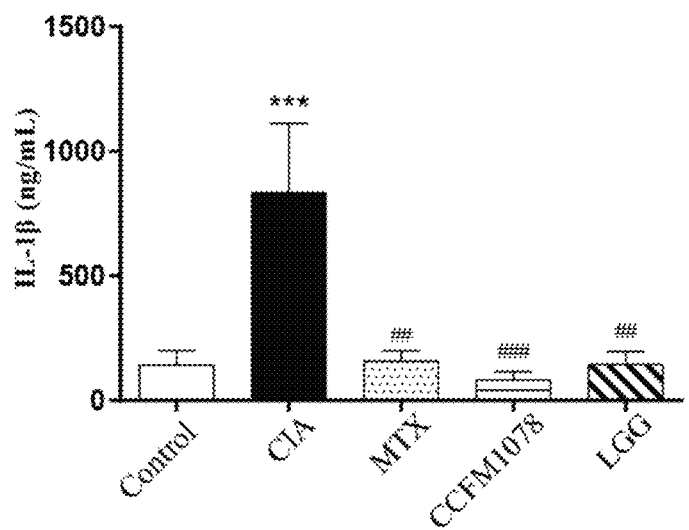
FIG. 6 shows the effect of the *B. breve* CCFM1078 on the level of TNFα in the serum of rats with rheumatoid arthritis.

As shown in FIG. 6, the level of TNFα in the serum of the rats in the model group was 14 ng/L, and was significantly higher than that in the normal group (9.8 ng/L). The levels of TNFα in the serum of the rats in the LGG group and the CCFM1078 group were 12 ng/L and 13 ng/L, respectively, and were lower than that of the rats in the model group. The level of TNFα in the serum of the rats in the drug group was 12 ng/L.

It can be seen that the *B. breve* CCFM1078 could reduce the levels of the pro-inflammatory factors IL-1β and TNFα in the serum of rats with rheumatoid arthritis, and especially the inhibitory effect on IL-1β was greater than those of the control bacteria LGG and the drug. The abilities of the CCFM1078, the LGG and the drug to inhibit the production of TNFα were equivalent.

Example 7: Effect of *B. breve* CCFM1078 on the Level of Anti-Inflammatory Factor IL-10 in the Serum of Rats with Rheumatoid Arthritis Sixty 7-week-old SPF (Specific Pathogen Free) female Wistar rats were raised at a room temperature of 22-24° C., a humidity of 40-60%, and an alternation of 12 h/12 h day and night. After being raised for 1 week under the condition of ad libitum, the rats were randomly divided into 5 groups with 12 rats in each group. The 5 groups were a normal group, a model group, a drug group administered with methotrexate by gavage, an LGG group administered with LGG by gavage, and a CCFM1078 group administered with *B. breve* CCFM1078 by gavage.

The experiment was started after the rats were adaptively raised for one week, and lasted for eight weeks. During the two weeks before modelling, each rat in the normal group, the drug group and the model group was administered by gavage with 1.5 mL of sterile normal saline with a concentration of 0.9 g/100 mL per day, each rat in the LGG group was administered by gavage with 1.5 mL of an LGG bacterial solution with a concentration of $5 \times 10^9$ CFU/mL per day, and each rat in the CCFM1078 group was administered by gavage with 1.5 mL of a *B. breve* CCFM1078 bacterial solution with a concentration of $5 \times 10^9$ CFU/mL per day. The third week to the fourth week was a modelling period. On the first day of modelling, a bovine type II collagen solution (Chondrex, 20022) and a Freund's incomplete adjuvant (Chondrex, 7002) were mixed in equal volumes and emulsified to form a complete emulsion (the emulsion was prepared for immediate use, and the prepared emulsion was used within 1 h). A rat was anesthetized with isoflurane and immobilized, the whole rat tail root was disinfected with 75% (v/v) alcohol, and then the rat was subjected to primary immunization. In the primary immunization, 0.15 mL of the complete emulsion was accurately pipetted and injected subcutaneously at 1.5 cm from the tail root of the rat. One week later, booster immunization was conducted by the same treatment method, that is, 0.15 mL of the complete emulsion was accurately pipetted and injected subcutaneously at 2.0 cm from the tail root of the rat. The rats in the normal group were injected with only the same volume of sterile normal saline by the same method. During the modelling until the end of the experiment, each rat in the normal group and the model group was administered by gavage with 1.5 mL of sterile normal saline with a concentration of 0.9 g/100 mL per day; the drug group was administered by gavage with methotrexate twice at a dose of 7.6 mg/kg based on body weight, and was administered with 1.5 mL of sterile normal saline with a concentration of 0.9 g/100 mL for the rest of the time; each rat in the LGG group was administered by gavage with 1.5 mL of an LGG bacterial solution with a concentration of $5\times10^9$ CFU/mL per day; and each rat in the CCFM1078 group was administered by gavage with 1.5 mL of a *B. breve* CCFM1078 bacterial solution with a concentration of $5\times10^9$ CFU/mL per day.

Four weeks after the booster immunization, blood was collected and the rats were sacrificed. The rat serum was collected, and the level of IL-10 in the serum of the rats in each group were determined by an ELISA kit. The detection results are shown in FIG. 7.

Figure 7:
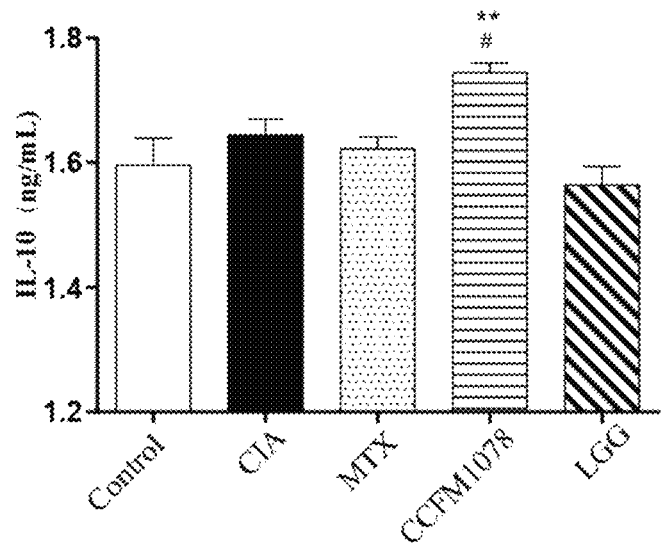
FIG. 7 shows the effect of the *B. breve* CCFM1078 on the level of IL-10 in the serum of rats with rheumatoid arthritis.
Figure 8:
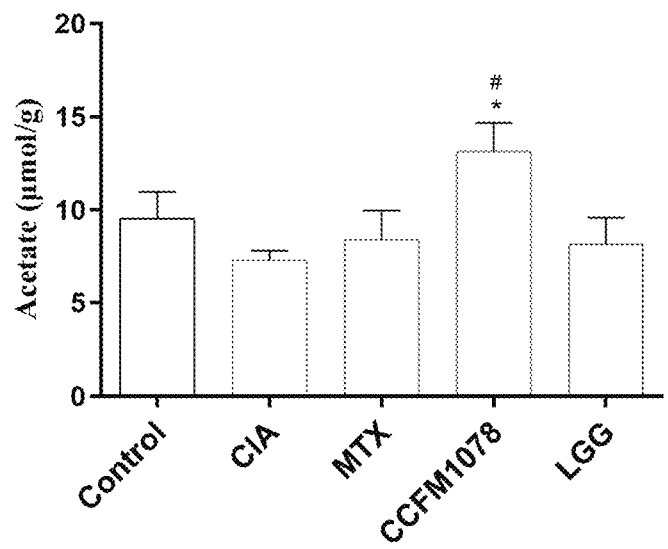
FIG. 8 shows the effect of the *B. breve* CCFM1078 on the content of acetic acid in the feces of rats with rheumatoid arthritis.
Figure 9:
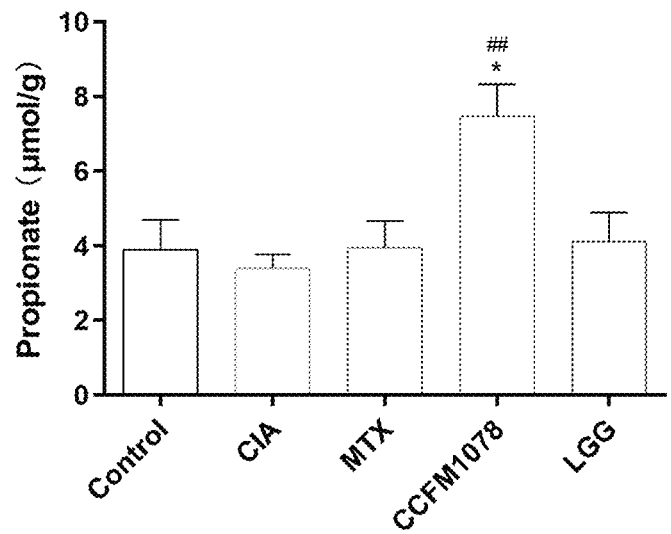
FIG. 9 shows the effect of the *B. breve* CCFM1078 on the content of propionic acid in the feces of rats with rheumatoid arthritis.
Figure 10:
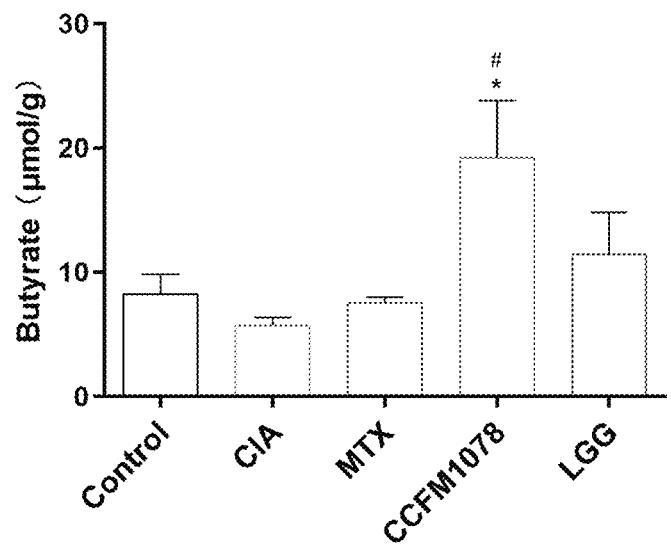
FIG. 10 shows the effect of the *B. breve* CCFM1078 on the content of butyric acid in the feces of rats with rheumatoid arthritis.
Figure 11:
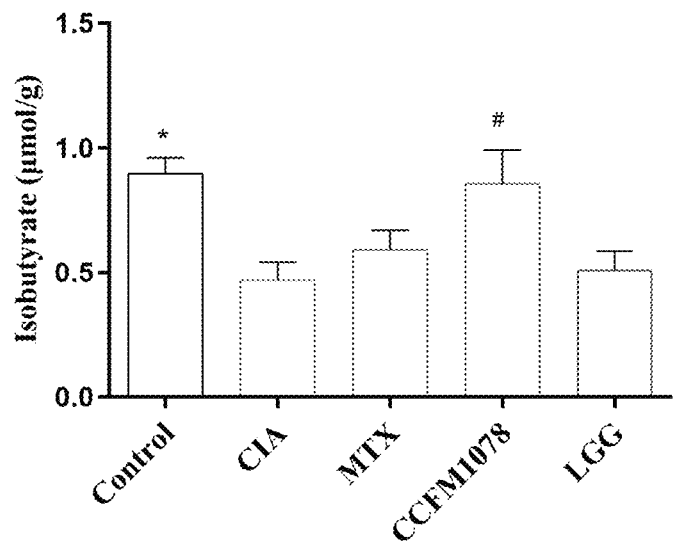
FIG. 11 shows the effect of the *B. breve* CCFM1078 on the content of isobutyric acid in the feces of rats with rheumatoid arthritis.
Figure 12:
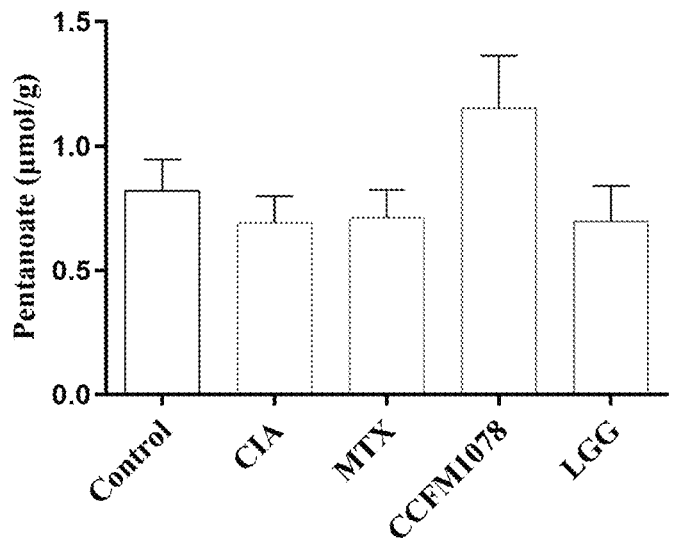
FIG. 12 shows the effect of the *B. breve* CCFM1078 on the content of pentanoic acid in the feces of rats with rheumatoid arthritis.

As shown in FIG. 7, the average concentration of IL-10 in the serum of the rats in the model group was 1.64 ng/L, and was similar to that of rats in the normal group (1.59 ng/L). Compared with the rats in the model group, the normal group and the LGG group, the level of IL-10 in the serum of the rats in the CCFM1078 group significantly increased (1.75 ng/L). The concentrations of IL-10 in the serum of the rats in the drug group and the LGG group were 1.62 ng/L and 1.56 ng/L respectively.

It can be seen that the *B. breve* CCFM1078 could promote production of the anti-inflammatory factor, and the promoting effect was significantly greater than those of the LGG and the drug methotrexate.

Example 8: Effect of the *B. breve* CCFM1078 on the Content of Short-Chain Fatty Acids in the Feces of Rats with Rheumatoid Arthritis Sixty 7-week-old SPF (Specific Pathogen Free) female Wistar rats were raised at a room temperature of 22-24° C., a humidity of 40-60%, and an alternation of 12 h/12 h day and night. After being raised for 1 week under the condition of ad libitum, the rats were randomly divided into 5 groups with 12 rats in each group. The 5 groups were a normal group, a model group, a drug group administered with methotrexate by gavage, an LGG group administered with LGG by gavage, and a CCFM1078 group administered with *B. breve* CCFM1078 by gavage.

The experiment was started after the rats were adaptively raised for one week, and lasted for eight weeks. During the two weeks before modelling, each rat in the normal group, the drug group and the model group was administered by gavage with 1.5 mL of sterile normal saline with a concentration of 0.9 g/100 mL per day, each rat in the LGG group was administered by gavage with 1.5 mL of an LGG bacterial solution with a concentration of $5\times10^9$ CFU/mL per day, and each rat in the CCFM1078 group was administered by gavage with 1.5 mL of a *B. breve* CCFM1078 bacterial solution with a concentration of $5\times10^9$ CFU/mL per day. The third week to the fourth week was a modelling period. On the first day of modelling, a bovine type II collagen solution (Chondrex, 20022) and a Freund's incomplete adjuvant (Chondrex, 7002) were mixed in equal volumes and emulsified to form a complete emulsion (the emulsion was prepared for immediate use, and the prepared emulsion was used within 1 h). A rat was anesthetized with isoflurane and immobilized, the whole rat tail root was disinfected with 75% (v/v) alcohol, and then the rat was subjected to primary immunization. In the primary immunization, 0.15 mL of the complete emulsion was accurately pipetted and injected subcutaneously at 1.5 cm from the tail root of the rat. One week later, booster immunization was conducted by the same treatment method, that is, 0.15 mL of the complete emulsion was accurately pipetted and injected subcutaneously at 2.0 cm from the tail root of the rat. The rats in the normal group were injected with only the same volume of sterile normal saline by the same method. During the modelling until the end of the experiment, each rat in the normal group and the model group was administered by gavage with 1.5 mL of sterile normal saline with a concentration of 0.9 g/100 mL per day; the drug group was administered by gavage with methotrexate twice at a dose of 7.6 mg/kg based on body weight, and was administered with 1.5 mL of sterile normal saline with a concentration of 0.9 g/100 mL for the rest of the time; each rat in the LGG group was administered by gavage with 1.5 mL of an LGG bacterial solution with a concentration of $5\times10^9$ CFU/mL per day; and each rat in the CCFM1078 group was administered by gavage with 1.5 mL of a *B. breve* CCFM1078 bacterial solution with a concentration of $5\times10^9$ CFU/mL per day.

Four weeks after the booster immunization, the rats were fasted with water for 12 h. Feces was collected and placed in liquid nitrogen, and then transferred into a −80° C. refrigerator. The feces were taken out before detecting the content of short-chain fatty acids, and freeze-dried by vacuum. 0.05 g of the freeze-dried feces sample was accurately weighed, dissolved in 0.5 mL of a saturated sodium chloride solution, soaked for 30 min, and homogenized by a tissue homogenizer. 0.02 mL of 10% sulfuric acid was added to the feces solution and the feces solution was shaken for 30 s. 0.8 mL of an ether solution was accurately added to the feces solution in a fume hood, and the feces solution was shaken for 30 s and centrifuged for 15 min (at 8000 g, 4° C.). The supernatant was pipetted into a centrifuge tube containing 0.3 g of anhydrous sodium sulfate, shaken evenly, and centrifuged for 15 min (at 8000 g, 4° C.). The supernatant was taken into a gas chromatography-mass spectrometry volumetric flask, and the content of short-chain fatty acids was detected by GCMS. The results are shown in FIGS. 8-12.

As shown in FIGS. 8-12, the contents of acetic acid, propionic acid, isobutyric acid, butyric acid, and pentanoic acid in the feces of rats in the model group decreased to 76.4%, 86.6%, 52.1%, 69.6% and 84.4% of those of rats in the normal group respectively, where the decrease in the isobutyric acid content was the most significant. The contents of acetic acid, propionic acid, isobutyric acid, butyric acid, and pentanoic acid in the feces of the rats in the CCFM1078 group were significantly up-regulated compared with the model group, were 13.16 μmol/g, 7.476 μmol/g, 0.857 μmol/g, 19.23 μmol/g and 1.152 μmol/g respectively, and were 1.8 times, 2.2 times, 1.8 times, 3.3 times, and 1.7 times those in the model group respectively. The contents of acetic acid, propionic acid, isobutyric acid, butyric acid, and pentanoic acid in the feces of the rats in the LGG group were 1.1 times, 1.2 times, 1.1 times, 2.0 times, and 1 time those in the model group respectively. The contents of acetic acid, propionic acid, isobutyric acid, butyric acid, and pentanoic acid in the feces of the rats in the drug group were 1.1 times, 1.2 times, 1.3 times, 1.3 times, and 1 time those in the model group respectively.

It can be seen that the *B. breve* CCFM1078 could generally increase the contents of short-chain fatty acids in the feces of rats with rheumatoid arthritis, the LGG could mainly increase the content of butyric acid in the short-chain fatty acids, and the recovery effect of the drug on the short-chain fatty acids was limited.

Example 9: Effect of the *B. breve* CCFM1078 on the Proportion of Th17 Cells in the Mesenteric Lymph Nodes of Rats with Rheumatoid Arthritis Sixty 7-week-old SPF (Specific Pathogen Free) female Wistar rats were raised at a room temperature of 22-24° C., a humidity of 40-60%, and an alternation of 12 h/12 h day and night. After being raised for 1 week under the condition of ad libitum, the rats were randomly divided into 5 groups with 12 rats in each group. The 5 groups were a normal group, a model group, a drug group administered with methotrexate by gavage, an LGG group administered with LGG by gavage, and a CCFM1078 group administered with *B. breve* CCFM1078 by gavage.

The experiment was started after the rats were adaptively raised for one week, and lasted for eight weeks. During the two weeks before modelling, each rat in the normal group, the drug group and the model group was administered by gavage with 1.5 mL of sterile normal saline with a concentration of 0.9 g/100 mL per day, each rat in the LGG group was administered by gavage with 1.5 mL of an LGG bacterial solution with a concentration of $5 \times 10^9$ CFU/mL per day, and each rat in the CCFM1078 group was administered by gavage with 1.5 mL of a *B. breve* CCFM1078 bacterial solution with a concentration of $5 \times 10^9$ CFU/mL per day. The third week to the fourth week was a modelling period. On the first day of modelling, a bovine type II collagen solution (Chondrex, 20022) and a Freund's incomplete adjuvant (Chondrex, 7002) were mixed in equal volumes and emulsified to form a complete emulsion (the emulsion was prepared for immediate use, and the prepared emulsion was used within 1 h). A rat was anesthetized with isoflurane and immobilized, the whole rat tail root was disinfected with 75% (v/v) alcohol, and then the rat was subjected to primary immunization. In the primary immunization, 0.15 mL of the complete emulsion was accurately pipetted and injected subcutaneously at 1.5 cm from the tail root of the rat. One week later, booster immunization was conducted by the same treatment method, that is, 0.15 mL of the complete emulsion was accurately pipetted and injected subcutaneously at 2.0 cm from the tail root of the rat. The rats in the normal group were injected with only the same volume of sterile normal saline by the same method. During the modelling until the end of the experiment, each rat in the normal group and the model group was administered by gavage with 1.5 mL of sterile normal saline with a concentration of 0.9 g/100 mL per day; the drug group was administered by gavage with methotrexate twice at a dose of 7.6 mg/kg based on body weight, and was administered with 1.5 mL of sterile normal saline with a concentration of 0.9 g/100 mL for the rest of the time; each rat in the LGG group was administered by gavage with 1.5 mL of an LGG bacterial solution with a concentration of $5 \times 10^9$ CFU/mL per day; and each rat in the CCFM1078 group was administered by gavage with 1.5 mL of a *B. breve* CCFM1078 bacterial solution with a concentration of $5 \times 10^9$ CFU/mL per day.

Four weeks after the booster immunization, the rats were anesthetized with isoflurane and blood was collected from the heart of the rats. The sacrificed rats were soaked in 75% alcohol for 15 min, and then taken out to isolate the mesenteric lymph nodes aseptically. The mesenteric lymph nodes were prepared into a single cell suspension with a cell concentration of $2 \times 10^6$ CFU/mL. A stimulant was added to the single cell suspension, and the single cell suspension was cultured and stimulated in a cell incubator at 37° C. for 6 h. The stimulated cells were stained on the surface with an CD4-FITC antibody, immobilized to permeabilize the membrane, and stained with IL-17A-PE intracellularly. The proportion of Th17 cells was detected by flow cytometry. The detection results are shown in FIG. 13.

Figure 13:
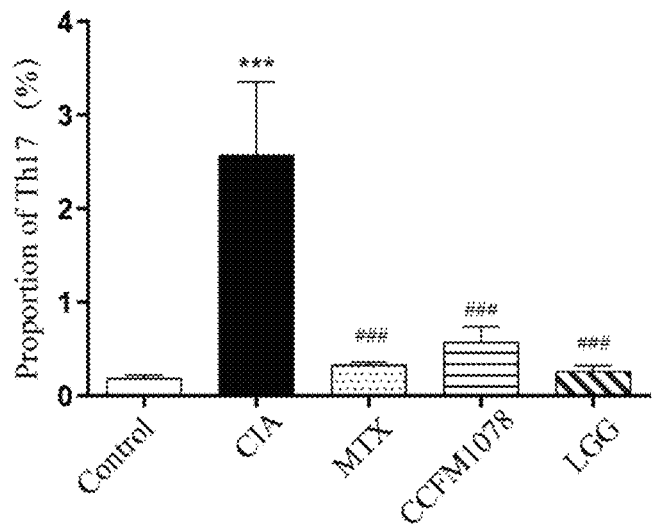
FIG. 13 shows the effect of the *B. breve* CCFM1078 on the proportion of Th17 cells in the mesenteries of rats with rheumatoid arthritis.

As shown in FIG. 13, compared with the rats in the normal group, the proportion of Th17 cells in the mesenteric lymph nodes of the rats in the model group increased significantly, and was 13.97 times that in the normal group. The proportion of Th17 cells in the mesenteric lymph nodes of the rats in the CCFM107 group and the LGG group decreased significantly, to as low as 22.2% and 10.0% of that in the model group respectively. The proportion of Th17 cells in the mesenteric lymph nodes of the rats in the drug group decreased to 12.7% of that in the model group.

It can be seen that rheumatoid arthritis could cause an imbalance in the proportion of Th17 cells in the rat mesentery, and the *B. breve* CCFM1078, the LGG and the drug methotrexate could significantly decrease the proportion of Th17 cells in the mesentery of rats with rheumatoid arthritis and make the proportion tend to be normal.

Example 10: Effect of *B. breve* CCFM1078 on the Secretion of Pro-Inflammatory Factor IL-6 from Synovial Cells The synovial tissue from the knee joint of the rats was taken and placed in a 10 cm cell culture dish, and washed with sterile PBS five times. After the tissue was cut with sterile dissecting scissors, the tissue was completely infiltrated in 3 mL of a DMEM complete medium containing collagenase (DEME: Type II collagenase=25:1, v/v), and digested in a cell incubator (at 37° C., 5% $CO_2$) for 6 h. After 6 h, 3 mL of pancreatin was added and cells were pipetted to stop the digestion, and primary cells were obtained. The primary cells were filtered through a cell strainer with a pore size of 70 μm, and the filtrate was collected and centrifuged at 1500 rpm for 5 min. The cells were resuspended in the DEME complete medium containing 10% (v/v) fetal bovine serum, and transferred into a 9 cm cell culture dish (37° C., 5% $CO_2$) for culture. In the culture process, the cell state was observed under a microscope. After 80% of the primary cells in the culture dish adhered to the wall, the medium in the culture dish was aspirated, and the cells were rinsed with a sterile PBS buffer three times. 2 mL of 0.25 g/100 mL pancreatin was added for digesting at 37° C. for 2 min, and the cells were gently pipetted. Finally, 2 mL of a DMEM complete medium containing 5% (v/v) fetal bovine serum was added to terminate the digestion, and a cell suspension A was obtained. The cell suspension A was centrifuged at 1000 rpm for 5 min, the supernatant was discarded, and bacteria were obtained. 10 mL of the DEME complete medium containing 10% (v/v) fetal bovine serum was added to the bacteria and pipetted evenly for counting, and the cell concentration was adjusted to $2 \times 10^6$ cells/mL with the DEME complete medium containing 10% (v/v) fetal bovine serum to obtain a cell suspension B.

MRS liquid media (containing 0.05 g/100 mL cysteine hydrochloride) were respectively inoculated with the *B. breve* CCFM1078 obtained in Example 1 and LGG and anaerobically cultured at 37° C. for 24 h, and then transferred into fresh MRS liquid media (containing 0.05 g/100 mL cysteine) and cultured at same conditions for 24 h. Bacteria were centrifuged at 6000 g for 15 min, washed with 0.9 g/100 mL normal saline, and centrifuged again at 6000 g for 10 min to obtain the bacteria. The bacteria of the *B. breve* CCFM1078 and the LGG were resuspended to a cell concentration of $5 \times 10^6$ cells/mL with DEME complete media, and complete DEME media containing the *B. breve* CCFM1078 and the LGG were obtained.

The cell suspension B was divided into four groups, namely a blank group, a positive control group, a CCFM1078 group and an LGG group. 1 mL of a DEME complete medium was added to the cell suspensions B in the blank group and the positive control group respectively, 1 mL of a DEME complete medium containing the *B. breve* CCFM1078 was added to the cell suspension B in the CCFM1078 group, and after 1 mL of a DEME complete medium containing the LGG was added to the cell suspension B in the LGG group, the cell suspensions were cultured in a cell incubator (37° C., 5% $CO_2$) for 4 h. 1 mL of a 200 ng/mL LPS solution was added to the cell suspensions B in the positive control group, the CCFM1078 group and the LGG group respectively, and after 1 mL of a DEME complete medium was added to the blank group, the cell suspensions B were cultured in a cell culture incubator (37° C., 5% $CO_2$) for 48 h to obtain culture solutions.

The culture solution was centrifuged to take the supernatant, and the level of IL-6 in the supernatant was determined. Determination was repeated six times for each group (see FIG. 14 for the determination results).

Figure 14:
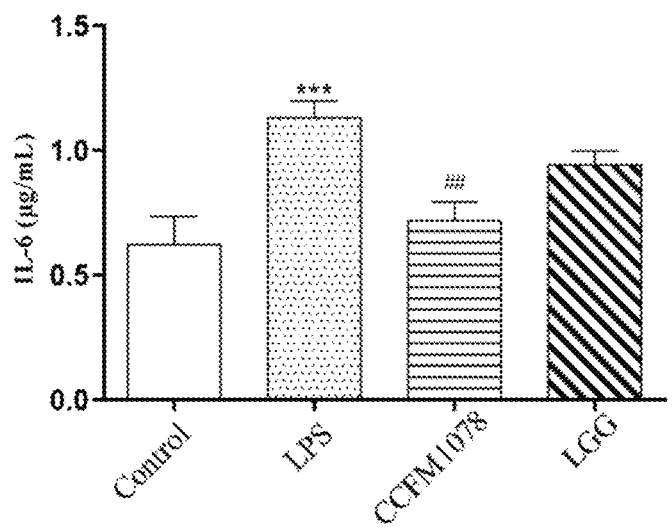
FIG. 14 shows the effect of the *B. breve* CCFM1078 on the secretion of IL-6 from synovial cells of rats with rheumatoid arthritis.

From FIG. 14, the level of IL-6 secreted by synovial cells significantly increased after LPS stimulation, and was 1.77 times that of the unstimulated group. After pretreatment with the *B. breve* CCFM1078 or the LGG, the level of IL-6 produced by the synovial cells decreased (to 0.72 ng/mL and 0.94 ng/mL, respectively). It was indicated that the *B. breve* CCFM1078 could inhibit secretion of the pro-inflammatory factor IL-6 from synovial cells in vitro, and the inhibitory effect was greater than LGG.

Example 11: Preparation of Freeze-Dried Bacterial Agent from *B. breve* CCFM1078

An MRS liquid medium (containing 0.05% cysteine) was inoculated with the *B. breve* CCFM1078 and anaerobically cultured at 37° C. for 24 h, and then transferred into a fresh MRS liquid medium (containing 0.05% cysteine) and cultured at same conditions for 24 h. Bacteria were centrifuged at 6000 g for 15 min, washed with 0.9% normal saline, and centrifuged again at 6000 g for 10 min. The bacteria were washed with a phosphate buffer with a pH of 7.2-7.4 3 times, and resuspended with a trehalose freeze-drying protectant with a trehalose concentration of 100 g/L (the mass ratio of the freeze-drying protectant to the bacteria was 2:1) to a concentration of $5 \times 10^{10}$ CFU/mL to obtain a resuspension. The resuspension was freeze-dried by vacuum freezing to obtain the freeze-dried *B. breve* CCFM1078 powder.

Rats with rheumatoid arthritis were administered with 1 g of the above freeze-dried powder by gavage per day for five weeks, and the symptoms of rheumatoid arthritis in the rats could be effectively relieved. Therefore, the freeze-dried powder has excellent effects in prevention and/or treatment of rheumatoid arthritis.

Example 12: Preparation of Food Product from *B. breve* CCFM1078

Preparation of fruit and vegetable beverages from *B. breve* CCFM1078

Fresh vegetables were washed and juiced, and the juice was subjected to high-temperature instant sterilization. After high-temperature sterilization was performed at 140° C. for 2 s, the temperature was immediately reduced to 37° C., and the juice was inoculated with a *B. breve* CCFM1078 bacterial starter prepared in Example 11 to make the concentration of *B. breve* CCFM1078 reach 10 6 CFU/mL or above, and was stored under refrigeration at 4° C., thereby obtaining a fruit and vegetable beverage containing the live *B. breve* CCFM1078 of the disclosure.

The disclosure can use the *B. breve* CCFM1078 to prepare other fermented food products by fermentation and production, and the fermented food products include solid food products, liquid food products, and semi-solid food products. The fermented food products include dairy products, bean products, and fruit and vegetable products; the dairy products include milk, sour cream, and cheese; and the fruit and vegetable products include cucumber, carrot, beet, celery, and cabbage products.

Example 13: Preparation of Drugs from *B. breve* CCFM1078

The *B. breve* CCFM1078 can be used to prepare liquid preparations, powders or tablets. The specific preparation process is as follows:

A single colony of the *B. breve* CCFM1078 obtained in Example 1 was picked, and an MRS liquid medium was inoculated with the single colony and cultured at 37° C. for 24 h to obtain an activated solution. An MRS liquid medium was inoculated with the activated solution according to an inoculation amount of 1% (v/v), and cultured at 37° C. for 24 h to obtain a primary seed solution. An MRS liquid medium was inoculated with the primary seed solution according to an inoculation amount of 1% (v/v), and cultured at 37° C. for 24 h to obtain a secondary seed solution. An MRS liquid medium was inoculated with the secondary seed solution according to an inoculation amount of 1% (v/v) and cultured at 37° C. for 24 h to obtain a bacterial solution. The bacterial solution was centrifuged at 6000 g for 15 min, and pellets were collected. The pellets were washed twice with a PBS buffer with a pH of 7.4, and then centrifuged at 6000 g for 10 min to obtain bacteria. The bacteria of *B. breve* were resuspended to a cell concentration of $1 \times 10^{10}$ CFU/mL with a protectant solution containing 130 g/L skim milk, 20 g/L trehalose, and 20 g/L sucrose to obtain a *B. breve* liquid preparation.

The *B. breve* liquid preparation prepared by the aforementioned method was freeze-dried to obtain a *B. breve* powder (agent).

Stearic acid as a lubricant accounting for 2% of the total weight of the *B. breve* powder and CMC-Na as a binder accounting for 3% of the total weight of the *B. breve* powder were added to the *B. breve* powder prepared by the aforementioned method, and tablet compressing was conducted to obtain tablets.

Rats with rheumatoid arthritis were administered with 1 mL of the above liquid preparation or 1 g of the above tablet by gavage per day for five weeks, and the symptoms of rheumatoid arthritis in the rats could be effectively relieved. Therefore, the liquid preparation or tablets have excellent effects in prevention and/or treatment of rheumatoid arthritis.

Although the disclosure has been disclosed as above in preferred examples, it is not intended to limit the disclosure. Those skilled in the art can make various changes and modifications without departing from the spirit and scope of the disclosure. Therefore, the protection scope of the disclosure should be defined by the claims.

What is claimed is:

1. A drug, comprising:
   freeze-dried *Bifidobacterium breve* (*B. breve*) CCFM1078; and
   a protective agent,
   wherein the *B. breve* is preserved at the Guangdong Microbial Culture Collection Center on May 6, 2020, with the preservation number GDMCC No: 61011,
   wherein the *B. breve* comprises an 16S rDNA sequence set forth in SEQ ID NO: 1 and a genome of 2.36 Mb, and a G+C content of 58.90%, and
   wherein the protective agent is selected from one or more of skim milk, trehalose, and sucrose.

2. The drug of claim 1, wherein the viable count of the *B. breve* in the drug is not less than $1 \times 10^5$ CFU/mL or $1 \times 10^5$ CFU/g.

3. A process for preparing the drug of claim 1, which comprises:
   inoculating an MRS liquid medium with the *B. breve*;
   culturing the bacteria anaerobically at 30° C. to 37° C;
   collecting bacterial cells;
   washing the bacterial cells with sterile normal saline;
   resuspending the bacterial cells with a freeze-drying protectant which comprises trehalose to a concentration $\geq 5 \times 10^{10}$ CFU/mL to obtain a resuspension; and
   freeze-drying the resuspension by vacuum freezing to obtain a freeze-dried *B. breve* powder.

4. The drug of claim 2, further comprising a drug carrier and/or pharmaceutical excipients.

5. The drug of claim 1, wherein upon administration of a pharmaceutically effective amount of the drug to a subject in need thereof by ingestion, the drug: (a) promotes secretion of IL-10 in the subject, (b) decreases serum levels of TNFα and IL-1β in the subject, (c) decreases a proportion of Th17 cells in feces of the subject, (d) reduced secretion of IL-6 from synovial cells of the subject, and/or (e) reduced joint thickness, clinical score, and incidence of rheumatoid arthritis in the subject, wherein the subject has or has been diagnosed with rheumatoid arthritis.

6. The drug of claim 1, further comprising one or more of: (i) dairy, (ii) beans, (iii) meat, and/or (iv) fruit.

* * * * *

SEQUENCE LISTING

<160> NUMBER OF SEQ ID NOS: 1

<210> SEQ ID NO 1
<211> LENGTH: 1437
<212> TYPE: DNA
<213> ORGANISM: Bifidobacterium breve

<400> SEQUENCE: 1

```
gagagtggcg aacgggtgag taatgcgtga ccgacctgcc ccatgcaccg gaatagctcc      60
tggaaacggg tggtaatgcc ggatgctcca gttgatcgca tggtcttctg ggaaagcctt     120
tgcggcatgg gatgggtcg cgtcctatca gcttgatggc ggggtaacgg cccaccatgg     180
cttcgacggg tagccggcct gagagggcga ccggccacat tgggactgag atacggccca     240
gactcctacg ggaggcagca gtggggaata ttgcacaatg ggcgcaagcc tgatgcagcg     300
acgccgcgtg agggatggag gccttcgggt tgtaaacctc ttttgttagg gagcaaggca     360
ttttgtgttg agtgtacctt tcgaataagc accggctaac tacgtgccag cagccgcggt     420
aatacgtagg gtgcaagcgt tatccggaat tattgggcgt aaagggctcg taggcggttc     480
gtcgcgtccg gtgtgaaagt ccatcgctta acggtggatc cgcgccgggt acgggcgggc     540
ttgagtgcgg tagggagac tggaattccc ggtgtaacgg tggaatgtgt agatatcggg     600
aagaacacca atgcgaagg caggtctctg gccgttact gacgctgagg agcgaaagcg     660
tggggagcga acaggattag ataccctggt agtccacgcc gtaaacggtg gatgctggat     720
gtggggcccg ttccacgggt tccgtgtcgg agctaacgcg ttaagcatcc cgcctgggga     780
gtacggccgc aaggctaaaa ctcaaagaaa ttgacggggg cccgcacaag cggcggagca     840
tgcggattaa ttcgatgcaa cgcgaagaac cttacctggg cttgacatgt tcccgacgat     900
cccagagatg gggtttccct tcggggcggg ttcacaggtg gtgcatggtc gtcgtcagct     960
cgtgtcgtga gatgttgggt taagtcccgc aacgagcgca accctcgccc cgtgttgcca    1020
gcggattgtg ccgggaactc acgggggacc gccggggtta actcggagga aggtggggat    1080
gacgtcagat catcatgccc cttacgtcca gggcttcacg catgctacaa tggccggtac    1140
aacgggatgc gacagcgcga gctggagcgg atccctgaaa accggtctca gttcggatcg    1200
cagtctgcaa ctcgactgcg tgaaggcgga gtcgctagta atcgcgaatc agcaacgtcg    1260
cggtgaatgc gttcccgggc cttgtacaca ccgcccgtca agtcatgaaa gtgggcagca    1320
cccgaagccg gtggcctaac cccttgcggg agggagccgt ctaaggtgag gctcgtgatt    1380
gggactaagt cgtaacaagg tagccgtacc ggaaggtgcg gctggatcac ctccttt      1437
```